United States Patent
Abutabl et al.

(10) Patent No.: US 12,316,802 B2
(45) Date of Patent: May 27, 2025

(54) METHOD FOR DRIVING AN EMERGENCY REACTION SYSTEM

(71) Applicant: Aptiv Technologies AG, Schaffhausen (CH)

(72) Inventors: Ahmed Abutabl, Wuppertal (DE); Prasant Narula, Wuppertal (DE)

(73) Assignee: Aptiv Technologies AG, Schaffhausen (CH)

( * ) Notice: Subject to any disclaimer, the term of this patent is extended or adjusted under 35 U.S.C. 154(b) by 386 days.

(21) Appl. No.: 17/659,110

(22) Filed: Apr. 13, 2022

(65) Prior Publication Data
US 2022/0337696 A1 Oct. 20, 2022

(30) Foreign Application Priority Data
Apr. 15, 2021 (EP) ..................................... 21168608

(51) Int. Cl.
*H04M 1/72421* (2021.01)
*A61B 5/00* (2006.01)
(Continued)

(52) U.S. Cl.
CPC ....... *H04M 1/72421* (2021.01); *A61B 5/0205* (2013.01); *A61B 5/0816* (2013.01);
(Continued)

(58) Field of Classification Search
None
See application file for complete search history.

(56) References Cited

U.S. PATENT DOCUMENTS

| | | | |
|---|---|---|---|
| 9,919,648 B1 * | 3/2018 | Pedersen | G06V 20/56 |
| 2016/0071418 A1 * | 3/2016 | Oshida | B60W 30/165 |
| | | | 701/23 |

(Continued)

FOREIGN PATENT DOCUMENTS

| | | | | |
|---|---|---|---|---|
| DE | 102015105581 | | 5/2016 | |
| DE | 102015105581 A1 * | | 5/2016 | ............. A61B 5/002 |

(Continued)

OTHER PUBLICATIONS

"Automotive-Binah", Retrieved at: https://web.archive.org/web/20180813123542/https://www.binah.ai/automotive/—on Apr. 11, 2022, 2 pages.

(Continued)

*Primary Examiner* — Adolf Dsouza
(74) *Attorney, Agent, or Firm* — Harness, Dickey & Pierce, P.L.C.

(57) ABSTRACT

A method is disclosed for driving an emergency reaction system within a moving motor vehicle carrying at least one vehicle occupant. The method includes monitoring health conditions of the vehicle occupant. The method also includes determining whether the health conditions are below a critical threshold and, if so, continuing to monitor the health conditions of the vehicle occupant. If the health conditions exceed the critical threshold, an emergency alert is issued without waiting for the motor vehicle to stop, and an autonomous safe stop maneuver is performed if the motor vehicle is moving autonomously or includes an autonomous driving system and is allowed to operate automatically.

18 Claims, 3 Drawing Sheets

(51) Int. Cl.
*A61B 5/0205* (2006.01)
*A61B 5/08* (2006.01)
*B60Q 9/00* (2006.01)
*B60W 60/00* (2020.01)
*H04M 1/72409* (2021.01)
*H04M 1/72457* (2021.01)

(52) U.S. Cl.
CPC .......... *A61B 5/4809* (2013.01); *A61B 5/6893* (2013.01); *B60W 60/0016* (2020.02); *H04M 1/724098* (2022.02); *H04M 1/72457* (2021.01); *A61B 2503/22* (2013.01); *B60Q 9/00* (2013.01); *B60W 2540/221* (2020.02)

(56) References Cited

U.S. PATENT DOCUMENTS

| | | | |
|---|---|---|---|
| 2020/0218257 A1 | 7/2020 | Raichelgauz et al. | |
| 2020/0317210 A1 | 10/2020 | Yang et al. | |
| 2023/0356728 A1* | 11/2023 | Jain | G06F 3/013 |

FOREIGN PATENT DOCUMENTS

| | | |
|---|---|---|
| KR | 20180108263 | 10/2018 |
| WO | 0020258 | 4/2000 |

OTHER PUBLICATIONS

"Extended European Search Report", EP Application No. 21168608.4, Sep. 1, 2021, 7 pages.

Leonhardt, et al., "Unobtrusive Vital Sign Monitoring in Automotive Environments—A Review", Sep. 2018, 38 pages.

Mercedes-Benz, "Introducing Drive Pilot: An Automated Driving System for the Highway:", Retrieved at: https://group.mercedes-benz.com/documents/innovation/other/2019-02-20-vssa-mercedes-benz-drive-pilot-a.pdf?r=dai—on Apr. 11, 2022, 54 pages.

Sidikova, et al., "Vital Sign Monitoring in Car Seats Based on Electrocardiography, Ballistocardiography and Seismocardiography: A Review", Oct. 2020, 28 pages.

* cited by examiner

METHOD FOR DRIVING AN EMERGENCY REACTION SYSTEM

CROSS-REFERENCE TO RELATED APPLICATION

This application claims priority to European Patent Application Number 21168608.4, filed Apr. 15, 2021, the disclosure of which is hereby incorporated by reference in its entirety.

BACKGROUND

Most of the vehicles in the current market do not include devices for measuring the vital signs of the vehicle occupants. In addition, the motor vehicles of the current market are unable to react on such signs in all standard situations in which the more vehicles may be present. As a result, there is a risk that a vehicle occupant may suddenly be confronted with a critical medial condition that may result in serious consequences not only for the vehicle occupant, but also for other road users, especially if the aforementioned vehicle occupant is the driver of the motor vehicle.

Systems for monitoring vital body signs of a seated person in a car are discussed in a paper entitled "*Vital Sign Monitoring in Car Seats Based on Electrocardiography, Ballistocardiography and Seismocardiography: A Review*" by Michaela Sidikova et al. and published on October 2020 through the Internet site of the National Center for Biotechnology Information (NCBI). The paper contains a background study on advanced signal processing methods and their potential application for the purpose of vital sign monitoring in cars, which is prone to various disturbances and artifacts occurrence that have to be eliminated.

Another known document is entitled "*Unobtrusive Vital Sign Monitoring in Automotive Environments—A Review*" by Steffen Leonhardt et al. and published on Sep. 13, 2018 through the Internet site of the Multidisciplinary Digital Publishing Institute (MDPI). The review provides an overview of unobtrusive monitoring techniques that could be used to monitor some of the human vital signs in a car seat.

As a further published document, the automotive manufacturer Daimler discloses on its Internet site a Level 3 conditional automated driving feature called "Drive Pilot" which secures the vehicle from rolling away and seeks aid by placing an emergency call to a dedicated response center and prepares the vehicle for emergency assistance by unlocking the doors.

Since the systems suggested above do not overcome the above-mentioned issues, there is a need for improving existing disclosures in order to at least partially overcome the aforementioned drawbacks. In particular, it is suitable to propose a new approach that is more efficient while being able to take into account the most standard situations in which the motor vehicle may be present in the road environment.

SUMMARY OF THE DISCLOSURE

The present disclosure relates to the field of automotive, more specifically to emergency reaction systems based on health conditions of occupants within a motor vehicle, such as autonomous, semi-autonomous or conventional vehicles. More specifically, the present disclosure relates to a method for driving an emergency reaction system within a moving motor vehicle carrying at least one vehicle occupant, as well as a non-transitory computer-readable medium, an emergency reaction system for implementing the method and a motor vehicle comprising such an emergency reaction system.

In aspects, a method for driving an emergency reaction system within a moving motor vehicle carrying at least one vehicle occupant is disclosed. The method comprises monitoring health conditions of the vehicle occupant. The method also includes determining whether the health conditions are below a critical threshold and, if so, continuing to monitor the health conditions of the vehicle occupant, otherwise: issuing an emergency alert without waiting for the motor vehicle to be stopped, and performing an autonomous safe stop maneuver if the motor vehicle is moving autonomously or includes an autonomous driving system and is allowed to operate automatically.

Due to the features of the above method, any deficiency in the vital signs of the vehicle occupant can be detected and an appropriate emergency alert can be issued instantaneously, namely without waiting for the vehicle to be stopped on an appropriated and safe place. Accordingly, valuable reaction time can thus be saved between the health failure detection of the vehicle occupant and the instant where the emergency alert is launched. Indeed, depending on the location of the vehicle and on the traffic intensity, it may be difficult to find an appropriate place to stop the motor vehicle without risking endangerment. It means that the time interval until the vehicle reaches a safe place to stop before launching the alert may be quite long, especially considering the urgency of the situation.

In addition, in the present disclosure, the emergency alert is not limited to dial an emergency phone call number but it may take several other ways such a warning the road users and the vehicle occupants, especially the other vehicle occupants if there are several. It may be particularly useful to alert road users if the vehicle occupant who is suddenly affected in his health is the driver or a passenger, especially the unique occupant of a motor vehicle driving in an autonomous mode. Due to the present disclosure, the other vehicles may be notified, e.g. via a message or a sign projected on the rear windshield for instance, that the motor vehicle carries a person who need medical assistance and, therefore, can immediately react accordingly. Notifying that the motor vehicle needs immediate medical attention also allows to prioritize such a case over other less critical cases. Such a feature may be particularly useful if the motor vehicle is involved in a pile-up for example.

Preferably, the emergency alert is independent from any parameter other that health conditions of the vehicle occupant. Due to such a feature, the priority can advantageously be focused on the life functions of the vehicle occupant.

In one embodiment, the emergency alert is issued to at least one of: an emergency service, any road user, any vehicle occupant, or at least one support person, such as a support person external to the motor vehicle.

According to one embodiment, the emergency alert is issued, or issued first, to the emergency service, to any road user and/or to any vehicle occupant if the vehicle occupant whose health conditions has reached the critical threshold is a driver of the motor vehicle.

Preferably, the emergency alert is issued to any road user and/or to any vehicle occupant in a continuous or repetitive basis, even if the motor vehicle has stopped.

In another embodiment, the emergency alert is issued via at least one of: a call and/or a sending of a message, an audible and/or visual indication played through a multimedia system of the motor vehicle, or displayable indication projected on the ground and/or on at least one window of the motor vehicle.

Preferably, the call and/or the message is issued to the emergency service and/or to the support person, and the audible and/or visual indication is notified to any vehicle occupant and/or road user.

In one embodiment, the health conditions of the vehicle occupant comprise at least one of the following: conscious or unconscious state, at least one eye or facial parameter, at least one heart or blood parameter, or respiratory rate.

In a further embodiment, the emergency alert comprises information relating to the health conditions of the vehicle occupant whose health conditions have at least reached the critical threshold.

The information further comprises a position (e.g. a current position) of the motor vehicle if the emergency alert is issued to at least one of the emergency service and the support person.

According to one embodiment, the health conditions of the vehicle occupants are monitored as soon as the vehicle occupant is aboard the motor vehicle and/or as soon as the motor vehicle is moving, in order to keep the health conditions up to date.

The present disclosure further relates to a non-transitory computer-readable medium comprising program instructions for causing a processor to execute the method according to any of the method embodiments or according to any possible combination of its embodiments.

The present disclosure also relates to an emergency reaction system for implementing the aforementioned method according to any of its embodiments or according to any possible combination of its embodiments, said emergency reaction system comprising: at least one monitoring device or first interface for connecting a monitoring device able to monitor health conditions of a vehicle occupant, at least one warning device or second interface for connecting a warning device able to generate an emergency alert, or a controller for managing at least the monitoring and warning devices in accordance with said method.

In one embodiment, the emergency reaction system further comprises a third interface for establishing a connection with an autonomous driving system and/or with a positioning device for determining the position of the motor vehicle.

The present disclosures finally also relates to a motor vehicle comprising an emergency reaction system according to any of its embodiments.

Other embodiments and advantages will be disclosed hereafter in the detailed description.

BRIEF DESCRIPTION OF THE DRAWINGS

The disclosure and the embodiments suggested in the present disclosure should be taken as non-limitative examples and will be better understood with reference to the attached Figures in which.

DETAILED DESCRIPTION

Figure 1:
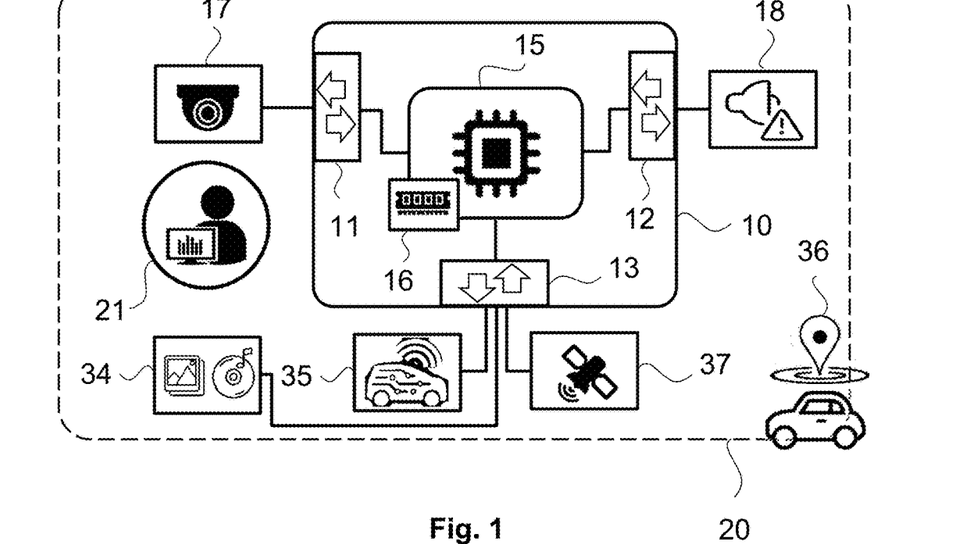
FIG. 1 mainly provides a schematic representation of an emergency reaction system, for implementing the method of the present disclosure, together with some motor vehicle peripheral devices that may be connected thereto.

FIG. 1 depicts a so-called emergency reaction system (ERS) 10, for implementing the method of the present disclosure, which is located within a motor vehicle 20 together with at least one vehicle occupant 21. The motor vehicle 20 that hosts the emergency reaction system may be a conventional vehicle, namely a vehicle which has no abilities to move in an autonomous manner, or may be a self-driving vehicle, i.e. an autonomous vehicle that is capable of sensing its environment and moving safely with little or no human input. As further alternative, the motor vehicle 20 may be a semi-autonomous vehicle, namely a motor vehicle located between the conventional or standard vehicle and the autonomous vehicle. The motor vehicle 20 can carry at least one vehicle occupant 21. Depending on the type of vehicle (conventional or autonomous), the vehicle occupant 21 may be the driver or a passenger of the motor vehicle 20. Since the autonomous vehicle can be switched between at least an autonomous mode and a manual mode, the vehicle occupant 21 sitting at the driver place may be regarded as a passenger if its motor vehicle is operating in the autonomous mode. Accordingly, the driver is regarded as being the vehicle occupant who is driving the motor vehicle, e.g. the person who is essential to ensure, at least at a certain time, the safe trip of the motor vehicle 20 until its next safe stop. In other words, if the motor vehicle 20 includes a driver seat that needs to be occupied for ensuring at least one maneuver of the moving motor vehicle 20 until its next safe stop, the vehicle occupant who is sitting on the drive seat is regarded as being the driver of the motor vehicle 20.

In FIG. 1, one can note that the emergency reaction system 10 may be connected to several devices 17, 18, 34, 35, 37 that may be regarded, at least for some of them, as peripheral devices 17, 18, 37. To this end, the emergency reaction system 10 includes at least one communication interface, in the present example three interfaces 11, 12, 13, to which at least one of these devices may be connected.

More specifically, the emergency reaction system 10 includes: at least one monitoring device 17, or first interface 11 for connecting such a monitoring device 17, which is able to monitor health conditions 1 (or at least one health condition 1) of a vehicle occupant 21, at least one warning device 18 or second interface 12 for connecting a warning device 18 able to generate an emergency alert 3, and a controller 15 for managing at least the monitoring and warning devices 17, 18 in accordance with the method of the present disclosure.

In the example of FIG. 1, the monitoring device 17 and the warning device 18 are located outside the emergency reaction system 10 and connected to the latter, more particularly to the controller 15, via the first and second interfaces 11, 12, respectively. However, in another embodiment, the aforementioned monitoring device 17 and warning device 18 may be located inside the emergency reaction system 10. The same may be applied to another device, if any.

The controller 15 is typically a processing unit or a chip set that is able to control any device connected to the emergency reaction system 10 and to send, receive or exchange data or commands with any system connected thereto. Accordingly, the controller 15 is especially able to execute any step of the method of the present disclosure. To this end, the controller 15 may further include a memory 16 storing an algorithm, routine, or computer program steps of the aforementioned method. Alternatively, the memory 16 may be located within the emergency reaction system 10 or may be connected to the controller 15 via any interface of the emergency reaction system 10.

In one embodiment, the emergency reaction system 10 further includes an interface, e.g. the third interface 13, for at least establishing a connection with an autonomous driving system 35 of the motor vehicle 20 and/or with a positioning device 37 for determining a position 36 (e.g. the current position 36), of the motor vehicle 20. Such an autonomous driving system 35 may be part of an electronic control unit (ECU) of the motor vehicle or may be connected to such an ECU. In the example shown in FIG. 1, the third interface 13 is further used to connect a multimedia system 34 in accordance with another embodiment which will be disclosed later.

It should be noted that any communication interface, with which the emergency reaction system 10 is equipped, may be a wired or wireless interface.

Figure 2:
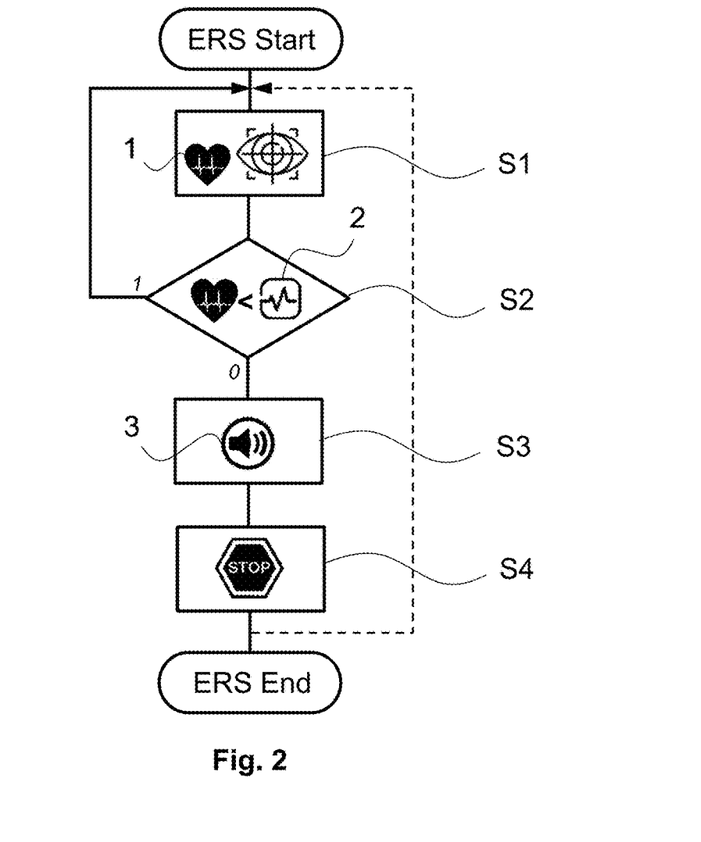
FIG. 2 is a flowchart of the method according to its main embodiment.

FIG. 2 provides a flowchart of the method according to its basic embodiment. The method aims to drive the emergency reaction system 10 embedded within the motor vehicle 20, especially within the moving motor vehicle which is carrying at least one vehicle occupant 21, as already mentioned in connection with FIG. 1.

The first step S1 aims to monitor health conditions 1 of the vehicle occupant 21. The health conditions 1 may be regarded as health parameters or health states of the vehicle occupant 21. The first step S1 may be executed by the controller 15 and carried out by using any type of detector or sensor, such as sensors located in the vehicle seat, in the steering wheel and/or in the seat belt for instance. Artificial intelligence including machine learning can be used through a camera system as part of a monitoring system including several physiological sensors installed in the motor vehicle 20 to monitor the health conditions 1 of the vehicle occupant 21. The camera system may include at least one camera (e.g. several cameras including at least one 360° camera). The cameras are used to monitor the faces of the vehicle occupant 21 in order to detect some facial behaviors for example.

The second step S2 aims to determine whether the health conditions 1 are below a critical threshold 2 and, if so, continuing to monitor the health conditions 1 of the vehicle occupant 21. The second step S2 may typically be performed by the controller 15 which can be in charge of the process execution for implementing the method. The positive output of the test shown through the diamond of step S2 in the flowchart of FIG. 1 is schematized by the value 1 and the negative output by the value 0. The health conditions 1 may measure several life functions through values that can each be compared with a threshold, especially a predefined critical threshold 2 from which it may be considered that the vehicle occupant 21 is in distress or puts his/her health at risk. If the health conditions 1, in particular the values of the measured life functions, are each below the critical threshold 2, the method or process of the emergency reaction system 10 does not take any specific action and therefore continues to monitor the health conditions 1 of the vehicle occupant 21. Otherwise, i.e. if the health conditions 1 reach or exceed the critical threshold 2, more particularly if at least one of the measured life function value is equal or above the critical threshold 2, the process leaves the loop between steps S1 and S2 and go to the third step S3.

The third step S3 aims to issue an emergency alert 3 without waiting for stopping the motor vehicle 20. Preferably, the emergency reaction system 10 triggers an emergency alert 3 as soon as the conditional operation set at the second step S2 causes a negative output. Advantageously, the system immediately reacts to any vital function deficiency of the vehicle occupant 21, thus saving precious seconds or minutes that allow to shorten the delay for the emergency intervention. As it is well known that such a delay may typically be decisive in case of heart attack for instance, triggering the emergency alert 3 without waiting for the motor vehicle 20 to stop can significantly contribute to save lives.

The fourth step S4 is a conditional step aiming to perform an autonomous or automatic safe stop maneuver if the motor vehicle 20 is moving autonomously or includes an autonomous driving system 35 and is allowed to operate automatically, at the present time. The four step S4 may be controlled by the emergency reaction system 10 and the safe stop maneuver may be performed by the autonomous driving system 35, if any. Several scenarios may be included in the fourth step S4. Indeed, a first sub-step may consist to determine whether the motor vehicle 20 is a conventional vehicle which is devoid of any automatic or autonomous driving system, or is provided with autonomous driving capabilities, such as an autonomous driving system 35. If the motor vehicle 20 is provided with such a system, the second sub-step may consist to determine whether the autonomous driving system 35 is currently operating and, if so, performing an autonomous safe stop maneuver as soon as possible. Otherwise, e.g. if the autonomous driving system 35 is not currently operating, a third sub-step may consist of determining whether the autonomous driving system 35 is allowed to operate.

Indeed, safe automated driving may depend on a set of predefined conditions under which the motor vehicle 20 can operate automatically. These set of conditions are also referred to as Operational Design Domains (ODD) by the person skilled in the art. For example, such conditions may be on a highway with limited access, during the daytime with no inclement weather and at certain speed. These conditions may also include predefined area, such as city centers, business parks or countryside areas, while avoiding allowing the autonomous mode to operate on a four-lane highway for instance. Therefore, if the autonomous driving system is allowed to operate automatically, e.g. if the ODD conditions are met, the system performs an autonomous safe stop maneuver. Otherwise, the motor vehicle 20 is considered as being a conventional vehicle. Such a state may be defined in a temporary way, in the sense that the emergency reaction system 10 may continuously or regularly check whether the ODD conditions are met and, if any, switch to the autonomous driving mode as soon as it is allowed to do so.

From the foregoing, it should be noted that issuing the emergency alert 3 is carried out regardless of the type of motor vehicle 20, e.g. whether it is a conventional or autonomous vehicle. Accordingly, such a feature further contributes to provide an efficient process for properly reacting face to emergency situations that may affect any vehicle occupant 21, given that it is advantageously not limited to motor vehicles 20 provided with autonomous capabilities.

In one embodiment, the emergency alert 3 is issued independently from any parameter other than health conditions 1 of the vehicle occupant 21. Accordingly, the method of the present disclosure is advantageously dedicated to the physiological parameters of the vehicle occupant 21 who is definitely the most precious entity which is part of the moving motor vehicle 20. By excluding any parameter other than health conditions 1 of the vehicle occupant 21, the reliability of the present method is advantageously increased, given that it is based on a limited number of parameters, thus reducing number of sensors, devices and/or connections that may fail, malfunction or cause a failure.

Figure 3:
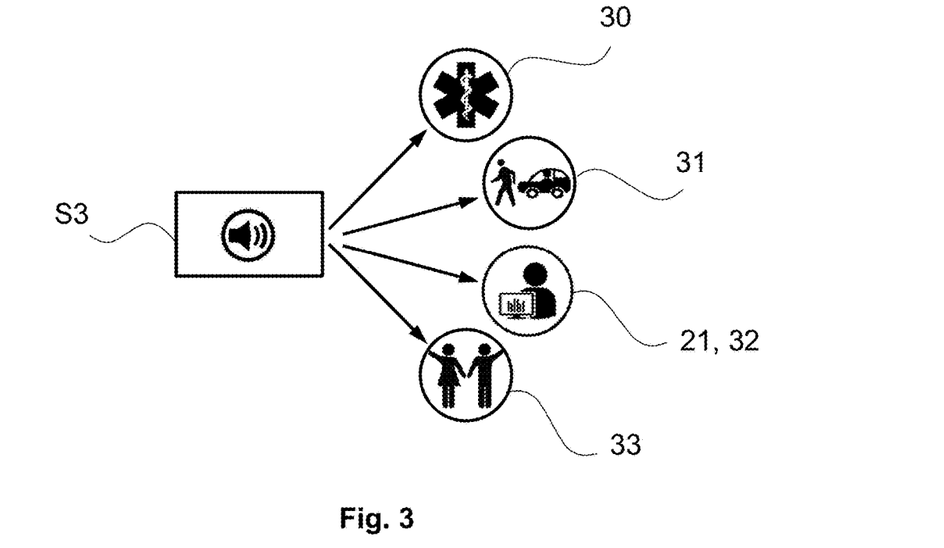
FIG. 3 is a schematic representation of several actors to whom the emergency alert may be issued.

With respect to another embodiment of the present method, FIG. 3 provides a schematic representation of several actors to whom the emergency alert 3 may be issued. More specifically, the emergency alert 3 is issued or notified to at least one of: an emergency service 30, any road user 31, any vehicle occupant 21 or other vehicle occupant 32, and at least one support person 33. The emergency service 30 may typically be a hospital, a medical cabinet, a medical hotline or an office or company providing emergency services e.g. in order to get an ambulance or a rescue team. The road user 31 can be any person in the vicinity of the motor vehicle 20, including persons in third vehicles, pedestrians, or rescue teams for example. The other vehicle occupant 32 refers to any vehicle occupant other than the vehicle occupant 21 who is at the origin of the emergency alert 3, in the event that the motor vehicle 20 includes more than one vehicle occupant 21. Finally, the support person 33 may be any trusted person of the vehicle occupant 21, such as a family member, a friend, or a guardian for example. Accordingly, the support person 33 is typically a person external to the motor vehicle 20 that may be reached using remote communication means.

Preferably, the emergency alert 3 is issued, or issued first, to at least one of the emergency service 30, any road user 31 and any other vehicle occupant 32. The emergency alert 3 may be issued to any other vehicle occupant 32 if the vehicle occupant 21 whose health conditions 1 has reached the critical threshold 2 is a driver of the motor vehicle 20. Due to this embodiment, the other vehicle occupant 32, if any, can immediately react in an attempt to avoid any accident, for instance by maintaining the steering wheel in the appropriate direction if the motor vehicle 20 is not operating in its autonomous driving mode or is a conventional motor vehicle 20. Furthermore, in the event that there is no vehicle occupant 21 other than the driver, the emergency service 30 may be automatically notified of the present critical situation, as well as the persons in nearby vehicles. Such a feature may be particularly useful, in the case where the vehicle occupant 21 who has triggered the emergency alert 3 is alone aboard a motor vehicle 20 which is currently moving under the control of the autonomous driving system. Indeed, in such a case, it would be difficult or even impossible for a person external to the motor vehicle 20 to be aware that the vehicle occupant 21 is currently seriously affected in his/her health and needs help. Therefore, the present disclosure allows to avoid such a situation that may be critical at least for the vehicle occupant 21.

The emergency alert 3 may be issued (or notified) to any road user 31 and/or to any other vehicle occupant 32 in a continuous or repetitive basis, even if the motor vehicle 20 has stopped. Such a feature may be especially useful, for example in the case where all the vehicle occupants 21 need help while none of them is able to call for help. Due to the aforementioned feature, people such as paramedics coming to the motor vehicle 20 once stopped may be immediately notified by the emergency driving system 10 of the vehicle occupant vital body parameters measured by physiological sensors or by any other monitoring device(s) 17 of the system.

Figure 4:
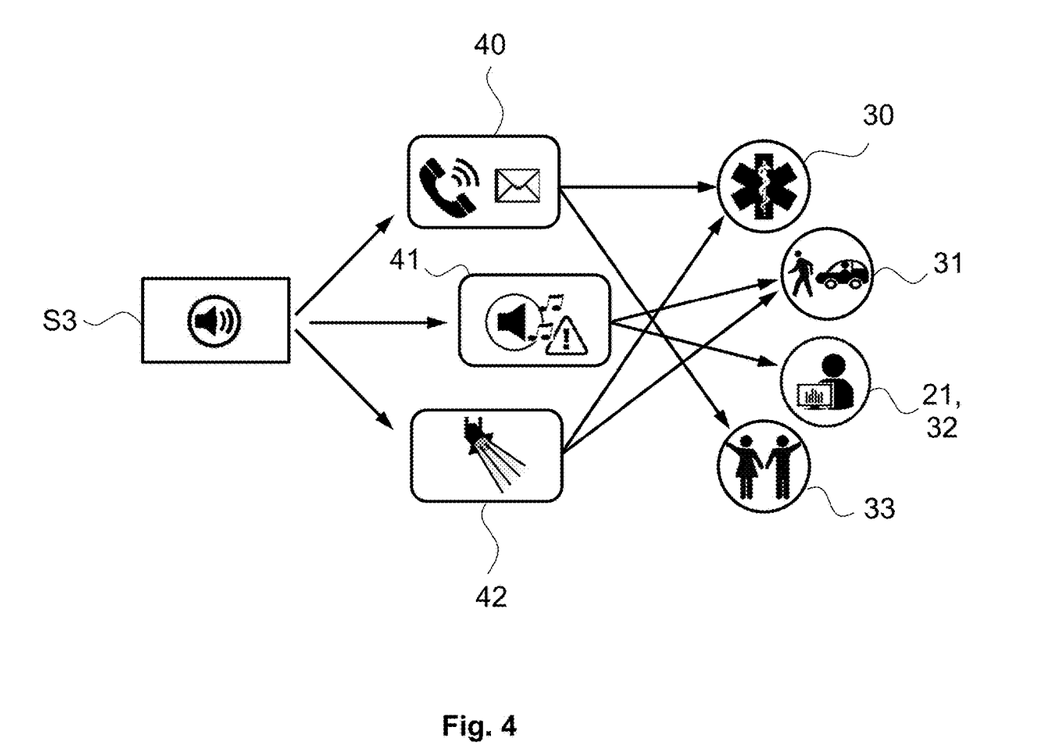
FIG. 4 is an explanatory diagram showing how the aforementioned actors may receive the emergency alert or may be notified accordingly.

FIG. 4 is an explanatory diagram showing how the different actors among the emergency service 30, the road user 31, the other vehicle occupant 32 and the aforementioned at least one support person 33 may receive the emergency alert 3 or may be notified accordingly. Indeed, the emergency alert 3 may be issued via several means that may be considered separately or in any combination.

As a first means, the emergency alert 3 may be issued through a call and/or the sending of a message 40. The call 40 may be a telephone call sent automatically by the emergency reaction system 10. The message can be not only a written message, such as a SMS, WhatsApp™ or any other instant message, but also a voice message. Both the call and the message may be sent via a cell phone network or any other available mobile communication network.

As second means, the emergency alert 3 may be issued via an audible and/or visual indication 41 (e.g. through a multimedia system 34 of the motor vehicle 20 that may be embedded therein). Typically, an in-car entertainment system may be used to notify or broadcast, through the display and/or the speakers of the entertainment system, the emergency alert 3 so that any person in the vicinity of the motor vehicle 20 can be alerted. Notifying such an emergency alert 3 using the entertainment or multimedia system 34 of the motor vehicle 20 may be performed in a continuous manner. In some aspects, the volume of the multimedia system 34 may be automatically increased at a predefined level to better broadcast the emergency alert 3.

As a third means, the emergency alert 3 may be issued in the form of a displayable indication 42 projected on the ground and/or on at least one window of the motor vehicle 20. The displayable indication 42 may typically be a message, a sign, or a pictogram that briefly and explicitly notify the emergency alert 3 to any person outside the motor vehicle 20.

Figure 5:
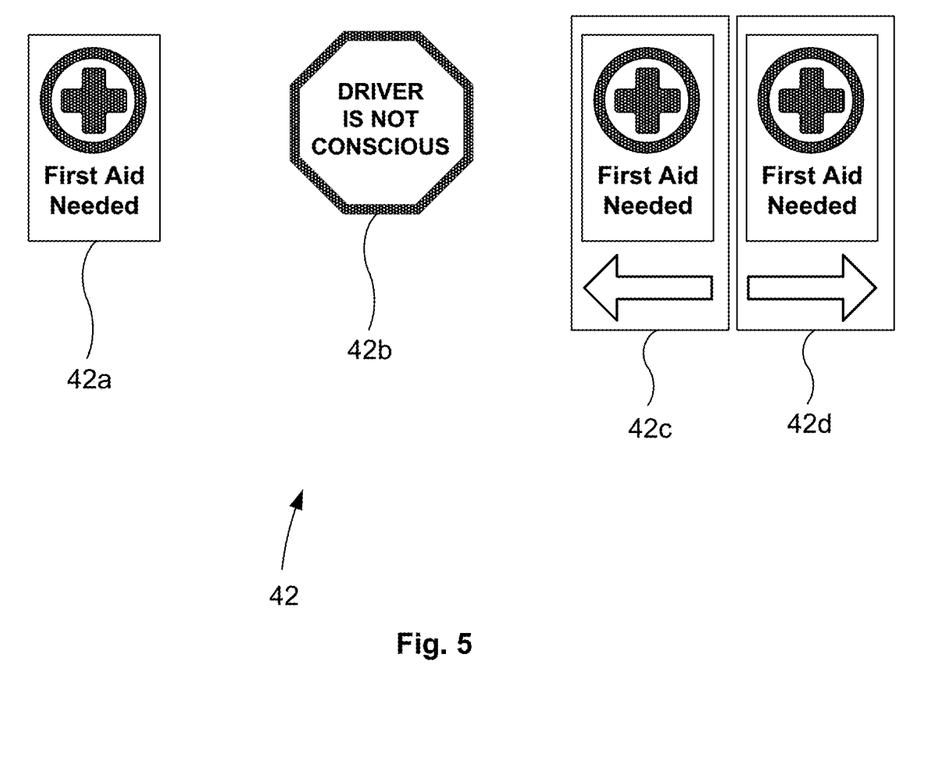
FIG. 5 provides sign examples that may be used as displayable indications for issuing or notifying the emergency alert.

FIG. 5 provides some examples, of messages signs or pictograms such as "First Aid Needed" sign 42a and "Driver is not conscious" sign 42b, that may be projected on the ground or on the rear windshield of the motor vehicle 20 for example. On the road, such a message or sign may be easily seen by any road users 31 such as persons within other vehicles and pedestrians, regardless the motor vehicle 20 displaying such an indication is moving or is stationary.

The displayable indication 42 may also be projected on the ground, i.e. on the road or on the side of the road, for example using LED projectors embedded in the motor vehicle 20. Such projectors may be located in the front of the motor vehicle 20, as head lamps, or below the doors which may include not only the side doors of the motor vehicle 20 but also the trunk door. Accordingly, these doors may not only be unlocked, but they may further be automatically opened by the emergency reaction system 10 in order to make the projection of the displayable indication 42 clearly visible on the ground, around the motor vehicle 20. For example, the sign 42c shown in FIG. 5 may be projected on the right side of the motor vehicle 20 and the sign 42d on its left side. The appropriate sign 42c, 42d to be projected may also depend on which side of the road the motor vehicle 20 is stopped on, or if the sign is rather intended to be seen from the rear or the front of the motor vehicle 20.

According to an embodiment shown in FIG. 4, the call and/or the message 40 is issued to the emergency service 30 and/or to the support person 33, and the audible and/or visual indication 41 is notified to any vehicle occupant 21 (e.g. other vehicle occupant 32) and/or road user 31. As further shown in FIG. 4, the audible and/or visual indication 41 is intended to any road user 31 and/or to any vehicle occupant 21, in particular to any other vehicle occupant 32, and the displayable indication 42 is intended to any road user 31 and to the emergency service 30, for example to the paramedics of the emergency service 30.

In one embodiment, the health conditions 1 of the vehicle occupant 21 include at least one of the following elements: conscious or unconscious state, at least one parameter related to the eye or face, at least one heart or blood parameter, such as heart rate, blood pressure, oxygen, or sugar blood level for example, and/or respiratory rate.

Other element or body responses may be taken into account such as, faster eye movement and blinking, some facial expressions, hand vibrations, change in skin color, skin temperature or skin conductivity resistance, or even alcohol level in blood or in exhalations of the vehicle occupant 21.

According to another embodiment, the emergency alert 3 includes information relating to the health conditions 1 of the vehicle occupant 21 whose health conditions 1 has reached the critical threshold 2. It means that the emergency alert 3 is not merely a warning sound or light, but includes and thus provides information regarding the emergency level of the vehicle occupant 21 who has caused the emergency alert 3. For example, the information of the emergency alert 3 may specify that first aid is need, as a low urgency level, and may specify that the vehicle occupant 21 is unconscious as a high urgency level. Other information may be provided for intermediate levels, if any. Furthermore, the emergency alert 3 may include further information, such as specific information regarding parameters, values, or other data of the health conditions 1 monitored by the physiological sensor(s) or monitoring device(s) 17. As example, the information may include the heart rate, the blood pressure, the oxygen level, or any other physiological or behavioral parameters of the vehicle occupant 21.

In aspects, the information further includes a position 36 (e.g. the current position or the most recent known position 36) of the motor vehicle 20, especially if the emergency alert 3 is issued to at least one of: the emergency service 30, and/or the support person 33.

To this end, the position (e.g. the current position 36 or location of the motor vehicle 20) may be provided by a positioning device 37, such as a Global Positioning System (GPS), which may be connected to the emergency reaction system 10, e.g. via one of the communication interface such as the third interface 13, as shown in FIG. 1. Alternatively, the positioning device 37 may be located within the emergency reaction system 10 and connected to an external antenna. Instead of a GPS module requiring the ability to receive satellite signals, the positioning device 37 may be based on a terrestrial radiolocation, e.g. on the radio signal(s) emitted by the mobile phone(s) of the vehicle occupant(s) 21. The radiolocation can be further based on trilateration between radio towers.

In one embodiment, the health conditions 1 of the vehicle occupants 21 are monitored as soon as the vehicle occupant 21 is aboard the motor vehicle 20 and/or as soon as the motor vehicle 20 is moving. Accordingly, the health conditions 1 of the vehicle occupant 21 can be advantageously kept up to date. Such an embodiment is schematically depicted by the two loops (one drawn in solid line and the other in dashed line) shown in FIG. 2 through the arrows which go back to the first step S1, respectively after the second step S2 and the fourth step S4. For example, such a monitoring may be based on a continuous or regular basis. Therefore, the information or at least of a part of the information included in the emergency alert 3 can be updated according to the most recent data provided by the monitoring operation performed at the first step S1. Furthermore, it may be possible to provide that a new call 40 and/or a new sending message 40 is triggered if the health conditions 1 reach a second threshold, e.g. a second predefined threshold that is higher than the first one which has been denoted as the critical threshold 2.

The present disclosure also relates to a non-transitory computer-readable medium 16 comprising program instructions for causing a processor, such as the controller 15 of FIG. 1, to execute the method according to any of its embodiments or according to any possible combination of its embodiments.

The term "non-transitory" does not exclude legitimate tangible temporary storage media such as flash drives or any rewritable storage media. Generally speaking, a computer-accessible medium may include any tangible or non-transitory storage media or memory media such as electronic, magnetic, or optical media. Such a media may be a disk, a CD/DVD-ROM or any other medium which may be coupled to the controller 15, e.g. via a dedicated communication interface or one of the already disclosed interfaces. Alternatively, such a media may be located within the controller 15, e.g. in a permanent manner.

The terms "tangible" and "non-transitory," as used herein, are intended to describe a computer-readable storage medium (or "memory") excluding propagating electromagnetic signals, but are not intended to otherwise limit the type of physical computer-readable storage device that is encompassed by the phrase computer-readable medium or memory. For instance, the terms "non-transitory computer-readable medium" or "tangible memory" are intended to encompass types of storage devices that do not necessarily store information permanently, including for example, random access memory (RAM) and flash memory. Program instructions and data stored on a tangible computer-accessible storage medium in non-transitory form may further be transmitted by transmission media or signals such as electrical, electromagnetic, or digital signals.

The present disclosure further relates to an emergency reaction system 10 for implementing the aforementioned method according to any of its embodiments or according to any possible combination of its embodiments. Since the emergency reaction system 10 has been already presented at the beginning of the detailed description and in connection with FIG. 1, it appears as being not useful to provide further details on such a device.

Finally, the present disclosure also relates to a motor vehicle 20 comprising at least the aforementioned emergency reaction system 10 according to any of its embodiments or possible combination of its embodiments.

Although an overview of the inventive subject matter has been described with reference to specific example embodiments, various modifications and changes may be made to these embodiments without departing from the broader spirit and scope of embodiments of the disclosure disclosed in the present description.

What is claimed is:

1. A method for operating an emergency reaction system within a moving motor vehicle carrying at least one vehicle occupant, the method comprising:
monitoring health conditions of the vehicle occupant by way of at least one of a vehicle seat sensor, a steering wheel sensor, a seat belt sensor and artificial intelligence through a camera system in the vehicle;
determining whether the health conditions are below a critical threshold;
responsive to the health conditions reaching or exceeding the critical threshold:

instantaneously issuing an emergency alert without seeking input from the vehicle occupant and without waiting for the motor vehicle to stop;
determining an appropriate place to stop the motor vehicle without risking endangering the motor vehicle; and
performing an autonomous safe stop maneuver if the motor vehicle is moving autonomously or activates an autonomous driving system that is allowed to operate automatically;
wherein the emergency alert is issued to at least one of an emergency service, a road user external to the motor vehicle, or at least one support person external to the motor vehicle.

2. The method of claim 1, wherein issuing the emergency alert is independent from parameters other than the health conditions of the vehicle occupant.

3. The method of claim 1, wherein the emergency alert is issued, or issued first, to the emergency service, to the road user, or to another vehicle occupant if the vehicle occupant whose health conditions have reached the critical threshold is a driver of the motor vehicle.

4. The method of claim 1, wherein the emergency alert is issued to the road user or to another vehicle occupant in a continuous or repetitive basis, even if the motor vehicle has stopped.

5. The method of claim 1, wherein the emergency alert is issued via at least one of:
a call or a sending of a message; or
displayable indication projected on a ground or on at least one window of the motor vehicle.

6. The method of claim 5, wherein the call or the message is issued to an emergency service or to a support person, and the audible or visual indication is notified to another vehicle occupant or a road user.

7. The method of claim 1, wherein the health conditions of the vehicle occupant comprise at least one of:
a conscious or unconscious state;
at least one eye or facial parameter;
at least one heart or blood parameter; or
respiratory rate.

8. The method of claim 1, wherein the emergency alert comprises information relating to the health conditions of the vehicle occupant whose health conditions have at least reached the critical threshold.

9. The method of claim 8, wherein the information further comprises a position of the motor vehicle if the emergency alert is issued to at least one of an emergency service or a support person.

10. The method of claim 1, wherein the health conditions of the vehicle occupant are monitored as soon as the vehicle occupant is aboard the motor vehicle or as soon as the motor vehicle is moving, in order to keep the health conditions up to date.

11. An emergency reaction system comprising:
a first interface for connecting to at least one monitoring device configured to monitor health conditions of a vehicle occupant of a motor vehicle, the at least one monitoring device selected from at least one of a vehicle seat sensor, a steering wheel sensor, a seat belt sensor and artificial intelligence through a camera system in the vehicle;
a second interface for connecting to a warning device configured to generate an emergency alert; and
a controller configured to manage the monitoring and warning devices to:
determine whether the health conditions are below a critical threshold;
responsive to the health conditions reaching or exceeding the critical threshold:
instantaneously issue an emergency alert without seeking input from the vehicle occupant and without waiting for the motor vehicle to stop;
determine an appropriate plate to stop the motor vehicle without risk of endangering the vehicle; and
perform an autonomous safe stop maneuver if the motor vehicle is moving autonomously or activate an autonomous driving system that is allowed to operate automatically;
wherein the emergency alert is issued to at least one of an emergency service, a road user external to the vehicle, or at least one support person external to the motor vehicle.

12. The emergency reaction system according to claim 11, further comprising a third interface for establishing a connection with an autonomous driving system or a positioning device for determining a position of the motor vehicle.

13. The emergency reaction system according to claim 11 wherein the emergency alert is issued, or issued first, to the emergency service, to the road user, or to another vehicle occupant if the vehicle occupant whose health conditions have reached the critical threshold is a driver of the motor vehicle.

14. The emergency reaction system according to claim 11, wherein the emergency alert is issued to the road user or to another vehicle occupant in a continuous or repetitive basis, even if the motor vehicle has stopped.

15. The emergency reaction system according to claim 11, wherein the emergency alert is issued via at least one of:
a call or a sending of a message; or
displayable indication projected on a ground or on at least one window of the motor vehicle.

16. The emergency reaction system according to claim 15, wherein the call or the message is issued to an emergency service or to a support person, and the audible or visual indication is notified to another road user.

17. The emergency reaction system according to claim 11, wherein:
the emergency alert comprises information relating to the health conditions of the vehicle occupant whose health conditions have at least reached the critical threshold; and
the information further comprises a position of the motor vehicle if the emergency alert is issued to at least one of an emergency service or a support person.

18. A non-transitory computer-readable medium comprising program instructions that, when executed by a processor, cause the processor to perform operations comprising:
monitoring health conditions of a vehicle occupant of a motor vehicle by way of at least one of a vehicle seat sensor, a steering wheel sensor, a seat belt sensor and artificial intelligence through a camera system in the vehicle;
determining whether the health conditions are below a critical threshold;
responsive to the health conditions reaching or exceeding the critical threshold:
instantaneously issuing an emergency alert without seeking input from the vehicle occupant and without waiting for the motor vehicle to stop;
determine an appropriate place to stop the motor vehicle without risk of endangering the vehicle; and performing an autonomous safe stop maneuver if the motor vehicle is moving autonomously or activating an autonomous driving system and is allowed to operate automatically;

wherein the emergency alert is issued to at least one of an emergency service, a road user external to the vehicle, or at least one support person external to the motor vehicle.

\* \* \* \* \*